(12) United States Patent
Segall et al.

(10) Patent No.: US 7,750,119 B2
(45) Date of Patent: Jul. 6, 2010

(54) PRODUCTION OF 2S CANOLA PROTEIN INVOLVING ION EXCHANGE

(75) Inventors: Kevin I. Segall, Winnipeg (CA); Martin Schweizer, Winnipeg (CA)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 0 days.

(21) Appl. No.: 12/185,181

(22) Filed: Aug. 4, 2008

(65) Prior Publication Data

US 2009/0036655 A1 Feb. 5, 2009

Related U.S. Application Data

(60) Provisional application No. 60/935,281, filed on Aug. 3, 2007.

(51) Int. Cl.
*C07K 1/18* (2006.01)
(52) U.S. Cl. ....................... 530/370; 530/416
(58) Field of Classification Search ....................... None
See application file for complete search history.

(56) References Cited

U.S. PATENT DOCUMENTS

| 2003/0125526 A1 | 7/2003 | Barker et al. |
| 2004/0034200 A1 | 2/2004 | Logie et al. |
| 2004/0039174 A1 | 2/2004 | Barker et al. |
| 2004/0254353 A1 | 12/2004 | Barker et al. |
| 2005/0181112 A1 | 8/2005 | Schweizer et al. |
| 2006/0121171 A1* | 6/2006 | Schweizer et al. .......... 426/590 |

FOREIGN PATENT DOCUMENTS

| WO | WO02/05922 | 1/2002 |
| WO | WO02/089597 | 11/2002 |
| WO | WO03/043439 | 5/2003 |
| WO | WO03/088760 | 10/2003 |
| WO | WO2005/067729 | 7/2005 |

OTHER PUBLICATIONS

Puumalainen et al (Napins, 2S albumins, are major allergens in oilseed rape and turnip rape J Allergy Clin Immunol. vol. 117, No. 2, pp. 426-432.*
Bérol, S. et al. Lare scale purification of rapeseed proteins (*Brassica napus* L.). Journal of Chromatography B. 2005, vol. 818, No. 1, pp. 35 to 42.

* cited by examiner

*Primary Examiner*—Manjunath N Rao
*Assistant Examiner*—Kagnew H Gebreyesus
(74) *Attorney, Agent, or Firm*—Michael I. Stewart; Sim & McBurney

(57) ABSTRACT

Substantially pure 2S canola protein is obtained substantially free from 7S and 12S canola protein by a procedure in which 2S canola protein is captured by binding to a cation-exchange medium while permitting other proteins and impurities to be washed away. The 2S canola protein then is removed from the cation-exchange medium by exposure of the cation-exchange medium to saline at a suitably high salt concentration.

6 Claims, No Drawings

PRODUCTION OF 2S CANOLA PROTEIN INVOLVING ION EXCHANGE

FIELD OF INVENTION

The present invention provides a procedure for the production of canola 2S protein in substantially pure form by a process involving the use of ion-exchange chromatography.

BACKGROUND TO THE INVENTION

Canola protein isolates having protein contents of at least 100 wt % (N×6.25) d.b. can be formed from canola oil seed meal, as described in co-pending U.S. patent application Ser. Nos. 10/137,391 filed May 3, 2002 (US Patent Application Publication No. 20030125526 A1), 10/476,230 filed Jun. 9, 2004 (US Patent Application Publication No. 20040254353 A1) and corresponding PCT Publication No. WO 02/089597, both assigned to the assignee hereof and the disclosures of which are incorporated herein by reference. The procedure involves a multiple step process comprising extracting canola oil seed meal using a salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous, gluten-like protein micellar mass (PMM), and recovering the protein micellar mass from supernatant having a protein content of at least about 100 wt % as determined by Kjeldahl nitrogen (N×6.25). As used herein, protein content is determined on a dry weight basis. The recovered PMM may be dried.

In one embodiment of the process described above, the supernatant from the PMM settling step is processed to recover a protein isolate comprising dried protein from the wet PMM and supernatant. This procedure may be effected by initially concentrating the supernatant using ultrafiltration membranes, mixing the concentrated supernatant with the wet PMM and drying the mixture. The resulting canola protein isolate has a high purity of at least about 90 wt % of protein (N×6.25), preferably at least about 100 wt % protein (N×6.25).

In another embodiment of the process described above, the supernatant from the PMM settling step is processed to recover a protein from the supernatant. This procedure may be effected by initially concentrating the supernatant using ultrafiltration membranes and drying the concentrate. The resulting canola protein isolate has a high purity of at least about 90 wt % protein (N×6.25), preferably at least about 100 wt % protein (N×6.25).

The procedures described in the aforementioned US patent applications are essentially batch procedures. In co-pending U.S. patent application Ser. No. 10/298,678 filed Nov. 19, 2002 (US Patent Application Publication No. 20040039174 A1) and corresponding published International Application No. WO 03/043439, assigned to the assignee hereof and the disclosures of which are incorporated herein by reference, there is described a continuous process for making canola protein isolates. In accordance therewith, canola oil seed meal is continuously mixed with a salt solution, the mixture is conveyed through a pipe while extracting protein from the canola oil seed meal to form an aqueous protein solution, the aqueous protein solution is continuously separated from residual canola oil seed meal, the aqueous protein solution is continuously conveyed through a selective membrane operation to increase the protein content of the aqueous protein solution to at least about 200 g/L while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is removed from the settling vessel and may be dried. The PMM has a protein content of at least about 90 wt % as determined by Kjeldahl nitrogen (N×6.25), preferably at least about 100 wt % (N×6.25).

As described in the aforementioned U.S. patent application Ser. Nos. 10/137,391 and 10/471,230, the overflowed supernatant may be processed to recover canola protein isolate therefrom.

Canola seed is known to contain about 10 to about 30 wt % proteins and several different protein components have been identified. These proteins are distinguished by different sedimentation coefficients (S). These known and identified proteins include a 12S globulin, known as cruciferin, a 7S globulin and a 2S albumin, known as napin.

Canola is also known as rapeseed or oil seed rape.

In co-pending U.S. patent application Ser. Nos. 10/413,371 filed Aug. 25, 2003 (US Patent Application Publication No. 20040034204) and 10/510,766 filed Apr. 15, 2003 as well as the corresponding published PCT Publication No. WO 03/08876, assigned to the assignee hereof and the disclosure of which is incorporated herein by reference, there is described the composition of the PMM canola protein isolate and of the supernatant-derived canola protein isolate. The supernatant-derived canola protein isolate is comprised predominantly of the 2S protein with smaller amounts of a 7S protein and a trace amount of 12S protein. The 2S protein is a low molecular weight albumin. The PMM product is comprised predominantly of the 7S protein with 2S protein and 12S protein being relatively minor components. The 7S and 12S protein are higher molecular weight globulins with the 7S molecule being the half molecule of the 12S protein.

As described therein, the supernatant-derived canola protein isolate exhibits a protein profile which is:
  about 60 to about 95% wt % of 2S protein,
  about 5 to about 40 wt % of 7S protein, and
  0 to about 5 wt % of 12S protein, preferably
  about 70 to about 95 wt % of 2S protein,
  about 5 to about 30 wt % of 7S protein, and
  0 to about 2 wt % of 12S protein.

The PMM canola protein isolate exhibits a protein profile which is:
  about 60 to about 98 wt % of 7S protein,
  about 1 to about 15 wt % of 12S protein, and
  0 to about 25 wt % of 2S protein, preferably
  about 88 to about 98 wt % of 7S protein,
  about 1 to about 10 wt % of 12S protein, and
  0 to about 6 wt % of 2S protein.

It has been found that the supernatant-derived canola protein isolate consisting predominantly of 2S protein exhibits superior functional properties for certain applications than the PMM-derived canola protein isolate consisting predominantly of 7S protein. In the procedures described in the prior applications, in order to produce the supernatant-derived canola protein isolate, it was necessary to go through the steps of PMM formation and provision of a supernatant in order, in effect, to fractionate the canola proteins.

In U.S. patent application Ser. No. 11/038,086 filed Jul. 21, 2005 (U.S. Patent Application Publication No. US 2005-

0181112 A1), assigned to the assignee hereof and the disclosure of which is incorporated herein by reference (WO 2005/067729), there is described a procedure in which the supernatant from the PMM precipitation is, before or after membrane processing, subjected to heat treatment to precipitate 7S protein and leave a protein solution enriched in 2S protein. The remaining solution may be spray dried to recover the 2S protein in dry form.

The 2S protein having a minimal proportion of the 7S and 12S proteins demonstrates increased solubility over the untreated 2S protein (including at acid pH values) and is able to provide improved clarity in aqueous solution and with soft drinks and sport drinks, providing clear protein fortified beverages.

SUMMARY OF THE INVENTION

The present invention utilizes an alternative procedure involving ion exchange to prepare substantially pure 2S canola protein substantially free from 7S and 12S canola proteins.

In ion exchange chromatography, charged ion-exchange medium is used to bind oppositely charged molecules while similarly charged and uncharged materials are not retained. This makes ion exchange chromatography a useful tool for purifying charged molecules, such as proteins. The two major classes of canola proteins have significantly different isoelectric points. The 7S/12S globulins have an isoelectric point in the range of about 6 to 7, while for the 2S albumin the value is approximately 11. This difference is utilized herein to separate the proteins from each other by ion exchange chromatography.

An ion exchange process is provided herein in which 2S protein is captured by binding it to the cation-exchange medium, while permitting other proteins and impurities to be washed away. The 2S protein then is released from the cation-exchange medium by exposure of the cation-exchange medium to saline at a suitably high salt concentration.

In accordance with one aspect of the present invention, there is provided a method of producing substantially pure 2S canola protein, which comprises solubilizing canola proteins from canola oil seed meal to form a canola protein solution, separating the canola protein solution from residual canola oil seed meal, contacting the canola protein solution with a cation-exchange medium under conditions wherein the 2S canola protein is bound to the cation-exchange medium in preference to other canola proteins, separating the bound 2S canola protein from unbound canola proteins and impurities, and separating the bound 2S canola protein from the cation-exchange medium.

GENERAL DESCRIPTION OF INVENTION

As mentioned above, ion-exchange chromatography is effected on canola protein solution to preferentially bind the 2S canola protein to the ion exchange medium and the 2S canola protein is subsequently recovered in substantially pure form from the ion exchange medium.

The procedure may be effected in any convenient manner. In one preferred aspect of the invention, an aqueous solution of canola protein is contacted with a cation exchange medium at a pH of about 5 to 6, where both classes of protein are positively charged. A salt concentration is utilized to limit binding of the less positively charged 7S/12S canola proteins as well as impurities, such as sinapine.

The aqueous canola protein solution may be most conveniently formed by extraction from canola oil seed meal. The extraction is effected using an aqueous salt solution having a desired saline concentration and pH value to be effective in ensuring preferential binding of 2S protein to the cation exchange medium. The salt solution generally has a salt concentration in the range of about 0.25 to 0.35 M NaCl and the pH of the aqueous canola protein solution is in the range of about 5 to about 6.

Extraction of the canola oil seed meal may be effected outside the desired pH range and the pH of the canola protein solution then may be adjusted to the pH range of about 5 to about 6 with any convenient acid or base, as necessary.

In an alternative, the protein may be extracted from the canola oil seed meal by using a saline solution of lower salt concentration and then additional salt is added to the desired concentration. However, it is preferred to effect the extraction with saline at the concentration required for the ion exchange, since the extract solution is in a form for direct application to the cation exchange medium for the isolation of the 2S canola protein immediately after formation. Therefore, there is little time for oxidation reactions to occur or the binding of phenolics to protein.

The canola protein extract solution is applied to the cation exchange medium, which may be provided in any convenient form, such as in the form of resin beads or a membrane adsorber. In a membrane adsorber, the ion exchange groups are bound to microporous membranes. The use of membranes instead of resin-packed columns allows the use of higher flow rates and results in faster processing.

The contact of the canola protein extract solution with the cation exchange medium, in the presence of the appropriate pH and salt level, causes the 2S protein to be adsorbed in preference to the less positively charged 7S/12S proteins. After separation of the cation exchange medium from the canola protein extract solution, the 2S protein may be removed from the cation exchange medium by contact with an aqueous saline solution having a higher salt concentration than that of the aqueous canola protein saline solution, such as about 0.55 to about 0.70 M NaCl.

The eluted solution of 2S protein has a high salt concentration and is desalted by any convenient manner, such as diafiltration, before drying the protein. The procedure produces a high purity 2S canola protein isolate substantially free from the 7S/12S proteins and having a protein content of at least about 100 wt % (N×6.25) on a dry weight basis (d.b.).

The canola 7S/12S proteins may be recovered from the canola protein extract after contact with the ion exchange medium in an undenatured form, in contrast to the form when isoelectric or heat precipitation are utilized to separate the proteins from 2S protein.

EXAMPLES

Example 1

This Example illustrates the preparation of substantially pure 2S canola protein using a cation exchange column.

(a) Protein Extraction:

A series of 15% w/v extractions of canola oil seed meal was carried out using typically 150 ml saline per 22.5 g meal. The samples were stirred for 30 minutes at room temperature using a magnetic stir bar. In each instance, the extract was separated from the spent meal by centrifugation at 10,200 g for 10 minutes and then further clarified by successive filtration with 25 µm pore size filter paper and 0.45 µm pore size syringe filters. The protein content of the clarified extract was determined by LECO analysis (LECO FP 528 Nitrogen Determinator) and the protein profile determined by size exclusion (SEC) HPLC. In the various runs, the salt concentration in the saline solution varied from 0.26 to 0.35 M NaCl.

As the extraction salt concentration was manipulated, this had some effect on the protein content and profile of the initial clarified extract (Table 1 below). The higher salt concentration was desirable in terms of protein yield and extraction of 2S protein, but had a negative impact on the separation, as seen below.

TABLE 1

Analysis of extracts prepared at different salt levels

| Concentration of NaCl (M) | pH | Protein conc. (%) | % HPLC protein peak area due to 2S |
|---|---|---|---|
| 0.26 | 5.60 | 2.62 | n.d.* |
| 0.29 | 5.67 | 2.71 | n.d.* |
| 0.30 | 5.61 | n.d.* | 36.9 |
| 0.35 | 5.61 | 2.82 | 37.4 |

*n.d. = not determined (b) Chromatography:

The samples were subjected to cation ion exchange (CIEX) chromatography using a SP Sepharose XL (20 ml) column operated using a GradiFrac LPLC system (Pharmacia Biotech) with peak collection enabled. In each run, 10 ml of clarified extract was applied to the column by way of a sample loop in the system. Under the saline concentrations employed, the 2S protein bound to the column while 7S and 12S canola proteins and other impurities passed through the column. The void material was captured and then saline at a higher salt concentration than the extract was applied to the column to release the bound 2S protein. The salt concentrations employed were adjusted as the runs proceeded in order to best separate the proteins and ensure the release of the bound material. A sample GradiFrac program used is shown in the following Table 2:

TABLE 2

Sample Gradifrac program for CIEX isolation of 2S from extract

| Volume (ml) | Conc. NaCl in buffer (M) | Buffer flow rate (ml/min) | Max. vol. fraction collected (ml) | Function |
|---|---|---|---|---|
| 0 | Extraction | 5 | 0 | Column equilibration |
| 19.9 | Extraction | 5 | 0 | |
| 20 | | Sample injection valve opened | | a) sample application |
| | Extraction | 5 | 25 | |
| 20 | | Sample injection valve closed | | b) 2S binding |
| 50 | Extraction | 5 | 25 | c) 7S/12S elution |
| 119.9 | | | | d) impurity elution |
| 120 | Elution | 5 | 25 | 2S elution |
| 194.9 | Elution | 5 | 25 | |
| 195 | 1.00 | 5 | 0 | Column cleaning |
| 254.9 | 1.00 | 5 | 0 | |
| 255 | Extraction | 5 | 0 | Column equilibration |
| 335 | Extraction | 5 | 0 | |

Note:
some minor variations in segment volume were employed as the method was developed.
Note:
once it was established that all of the 2S protein was released in the elution step, the cleaning of the column with 1M NaCl between runs was eliminated.

Each day, the eluted fractions from all runs were combined and frozen at −60° C. except for the product of runs 20 to 26, which was refrigerated for desalting the next day. The following Table 3 sets forth the salt concentrations used for extractions and elution in various production runs.

TABLE 3

Salt concentrations used for extractions and 2S protein elution in various production runs

| Production runs | Concentration NaCl in extraction (M) | Concentration of NaCl for 2S elution (M) |
|---|---|---|
| 1 | 0.30 | 0.55 |
| 2 | 0.30 | 0.60 |
| 3 to 8 | 0.35 | 0.65 |
| 9 to 13 | 0.29 | 0.65 |
| 14 to 26 | 0.26 | 0.65 |

The concentration of salt used for the extraction/protein separation and the elution of the 2S protein were fine tuned as the production runs proceeded. In the first run, the salt concentrations used were 0.30M/0.55M. The void material was collected as overlapping doublet peaks, with the first peak found to contain almost all of the 7S/12S, a small amount of unbound 2S protein and most of the impurities seen in the extract except a portion of the sinapine. The second peak in the doublet, which took slightly longer to emerge from the column, was found to contain a notable amount of sinapine and very small amounts of protein and other impurities. Elution with 0.55M NaCl failed to elute all of the 2S protein from the column as a notable 2S protein peak was obtained when cleaning the column with 1M NaCl.

For the second run, the elution salt level was raised to 0.60M to better release the 2S protein. This time a smaller 2S protein peak was found when the column was cleaned. In the third run, the elution step was increased to 0.65M NaCl and this level was found to effectively eliminate the peak seen when cleaning the column. The initial salt level in the third trial was increased to 0.35M NaCl in the hopes of bringing the two void peaks closer together. The separation between the doublet peaks was reduced, but a doublet was still obtained. Also, operating at this higher salt level increased the amount of 2S protein that did not bind the column and was found in the void.

Subsequently, the initial salt level was reduced to 0.29M, then 0.26M, successively reducing the level of 2S protein lost to the void (Table 4 below). It was feared that reducing this initial salt level would result in some binding of 7S/12S proteins or sinapine to column, which would be highly undesirable as it would complicate the 2S elution step. However, at 0.26M NaCl, 2S protein was the only species observed to bind to the column.

TABLE 4

2S content of the total void material based on extract salt concentration

| Concentration of NaCl (M) | Peak area 2S (counts) |
|---|---|
| 0.26 | 66769 |
| 0.29 | 115540 |
| 0.30 | n.d.* |
| 0.35 | 224545 |

*n.d. = not determined (c) Desalting of Eluted 2S Protein:

Frozen samples of eluted 2S protein were placed in the refrigerator overnight to thaw. The next day the still frozen containers were placed in a warm water bath, in which the samples were warmed just until the ice crystals were melted. All the thawed samples were then filtered through 25 μm pore size filter paper and combined into a single large sample. The resulting 2S protein solution was desalted by concentration and diafiltration on a Vivaflow 5000 MWCO Hydrosart ultrafiltration membrane unit. The total volume of the collected 2S protein fractions was approximately 1500 ml. The combined 2S protein solution was concentrated down to 25 to 30 ml and then 300 ml of water was added for diafiltration. The sample was reconcentrated to 25 to 30 ml, and a further 300 ml of water was added and then the sample reconcentrated again. As can be seen from the results contained in the following Table 5, the desalting was conducted effectively with two steps of approximately 10 diafiltration volumes.

TABLE 5

Reduction in salt content with diafiltration

| 2S Sample | Cond. (mS) | pH | Protein conc. (%) |
|---|---|---|---|
| Combined GradiFrac fractions | 49.6 | 5.83 | 0.31 |
| After adding DF1 water | 5.68 | 5.28 | n.d.* |
| After adding DF2 water | 0.943 | 4.92 | n.d.* |
| Final retentate | n.d.* | n.d.* | 5.84 |

*n.d. = not determined

The retentate then was freeze dried.

(d) Final Product:

The dry colour of the final product was assessed using a Minolta CR-310 Chroma meter and a solution was also prepared for wet colour analysis. Protein powder (0.5 g) was combined with water (10 ml) using a vortex mixer. The sample was then centrifugated at 7800 g for 10 min (mainly to remove air) and the protein content of the supernatant determined by LECO. An aliquot (8 ml) of the supernatant was transferred to a small beaker and sufficient water was added to adjust the protein content to 5%. The sample was then photographed and an aliquot of the sample used for protein profile analysis (SEC HPLC). Some sample was also diluted to 3.5% protein and another photograph taken. The protein content of the dry powder was tested by LECO but there was not enough sample obtained to do a moisture content analysis. Therefore, the protein content was only expressed on a wet basis.

A total of 1.63 g of final product was collected in this study. The protein content of the powder on a wet basis was 105.82% w/w (N×6.25). If expressed on a dry basis, as is the standard, then the protein content would be even higher. Chromatographic analysis of the re-hydrated product suggested that 96.1% of the peak area detected at 280 nm was attributable to 2S and 3.8% of the peak area was due to pro-napin. Therefore, 99.9% of the peak area was due to the protein of interest. No 7S or 12S protein was detected.

The colour scores for the dry product are shown in Table 6.

TABLE 6

Dry colour of 2S isolated from extract by cation exchange

| Sample | L* | a* | b* |
|---|---|---|---|
| 2S | 83.05 | −2.61 | 15.49 |

The wet colour of the product re-hydrated in water exhibited a greenish tinge and the clarity of the solution was excellent. It is thought that with the complete absence of 7S/12S proteins that the clarity of the solution should remain quite stable in most conditions.

The yield of the product seemed quite good. It was difficult to calculate a representative yield as the separation conditions were modified a number of times and 2S protein losses were known to occur, particularly in the initial runs, due to incomplete binding to the resin and also incomplete elution. By the last runs, all 2S protein was eluted but there was still a small amount that was not binding the column. As mentioned above, reducing the initial salt content may solve this problem provided that it does not allow other species to bind the column. If one considers that 1.63 g of 2S protein was generated from 260 ml (26×10 ml injections) of clarified extract, then this can be extrapolated to 6.3 kg of 2S from 1000 L of clarified extract.

Example 2

This Example illustrates the use of a cation exchange membrane to produce substantially pure 2S canola protein.

(a) Protein Extraction:

10% w/v extractions of 30 g of canola oil seed meal were effected using 300 ml of 0.3M NaCl by combining the meal and saline and stirring the samples for 30 minutes at room temperature using a magnetic stir bar. The extract was then separated from the spent meal by centrifugation at 10,200 g for 10 minutes and further clarified by successive filtration with 25 μm pore size filter paper and 1 μm and 0.45 μm pore size filter disks. The protein profile of the extract was determined by SEC HPLC.

0.26M NaCl was identified in Example 1 as the best choice of salt level for the extraction solution. This salt level was initially adopted in preliminary experiments with the membrane adsorber (data not shown), but small amounts of 7S/12S proteins and some sinapine were found to be bound by the membrane. Increasing the salt content of the extraction solution to 0.3M NaCl limited the 7S/12S proteins binding. The protein profile of the 0.3M NaCl extract was 64.6% of protein peak area due to 7S/12S and 35.4% due to 2S.

(b) Ion Exchange:

Ion exchange separations were performed using two Sartobind S75 (Sartorius AG, Goettingen, Germany) strong acidic cation adsorber membrane units joined in series. A peristaltic pump was used to push the various solutions through the membrane units. A sample separation protocol is shown in Table 7.

TABLE 7

Sample protocol for the isolation of 2S from extract using cation exchange membrane adsorber

| Step | Solution | Volume (ml) | Flow rate (ml/min) |
|---|---|---|---|
| Equilibration | 0.3M NaCl | 40 | 20 |
| Sample loading | Clarified extract | 10 | 20 |
| Membrane rinsing | 0.3M NaCl | 50 | 20 |
| 2S elution | 0.67M NaCl | 30 | 20 |

Approximately 32 runs were completed over the course of two consecutive days. Each day the eluted 2S protein fractions from all runs were combined and refrigerated until desalting. Protein profiles of the void/rinse and eluted fractions were delivered by SEC HPLC.

A small proportion of 2S (7.7% of protein peak area) was found to be lost to the void fraction, perhaps due to overloading of the system. The eluted fractions were almost entirely 2S (99.6% of the protein peak area). In the first day of production runs, 0.65M NaCl was used as the elution buffer and at the end of the day, the membrane adsorbers were cleaned with 1M NaCl (40 ml). Analysis (SEC HPLC) of the 1M NaCl eluate showed a small amount of 2S that had not been eluted by the 0.65M NaCl. For the second day of separation runs, 0.67M NaCl was used as the elution buffer. Cleaning the membranes with 1M NaCl did not release any 2S protein, indicating that 0.67M NaCl was sufficient to recover all of the bound 2S protein.

(c) Desalting of Isolated 2S Protein:

Eluted 2S protein was desalted by concentration and diafiltration on a Vivaflow 5000 MWCO Hydrosart ultrafiltration membrane unit. The volume of all the collected 2S protein fractions was approximately 1000 ml. This was concentrated down to 25 to 30 ml and then 300 ml of water was added for diafiltration. The sample was reconcentrated to 25 to 30 ml and a further 400 ml of water was added and the sample reconcentrated again. After the second diafiltration step, the retentate was freeze dried.

The conductivity of various samples was measured using a conductivity meter. The goal of diafiltration was to reduce the conductivity of the sample below 1 mS. The permeates were checked for protein profile by SEC HPLC.

The two diafiltration steps effectively reduced the conductivity of the 2S protein sample (Table 8). No protein was detected in the ultrafiltration or diafiltration permeates.

TABLE 8

Reduction in salt content with diafiltration

| 2S Sample | Conductivity (mS) |
| --- | --- |
| Eluate | 49.8 |
| After adding DF1 water | 7.56 |
| After adding DF2 water | 0.79 |
| Final retentate | n.d.* |

*n.d. = not determined (d) Final Product:

The dry colour of the final product was assessed using a Minolta CR-310 Chroma meter and a solution was also prepared for wet colour analysis. Protein powder (0.6 g) was combined with water (10 ml) using a vortex mixer. The sample was then centrifuged at 7800 g for 10 minutes and the protein content of the supernatant determined by LECO. An aliquot (8 ml) of the supernatant was transferred to a small beaker and sufficient water was added to adjust the protein content to 5%. The sample was then photographed and an aliquot of the sample used for protein profile analysis (SEC HPLC). Some sample was also diluted to 3.5% and another photograph taken. The protein content of the dry powder was tested by LECO but not enough sample was obtained to do a moisture content analysis. Therefore, the protein content was only expressed on a wet basis.

A total of 1.54 g of the final product was collected in this study. The purity of the product was very good with the protein content of the powder on a wet basis 101.99% w/w (N×6.25). As mentioned earlier, not enough sample was generated to perform moisture content analysis and therefore the protein content cannot be expressed on a dry basis. Chromatographic analysis of the rehydrated product indicated that 99.85% of the peak area detected at 280 nm was attributable to 2S protein. No 7S protein or 12S protein was detected.

The dry colour values determined for the membrane adsorber 2S are shown in Table 9.

TABLE 9

Dry colour of 2S isolated from extract by membrane adsorber cation exchange

| Sample | L* | a* | b* |
| --- | --- | --- | --- |
| 2S | 84.21 | −2.40 | 15.09 |

The wet colour and the clarity of the product re-hydrated in water was reminiscent of the 2S protein produced by column chromatography. It is thought that with the complete absence of 7S/12S proteins that the clarity of the solution should remain quite stable in most conditions.

SUMMARY OF THE DISCLOSURE

In summary of this disclosure, the present invention provides a method of recovering high purity 2S canola protein using ion exchange chromatography. Modifications are possible within the scope of this invention.

What we claim is:

1. A method of producing substantially pure 2S canola protein, consisting the steps of:
    solubilizing canola proteins from canola oil seed meal with an aqueous saline solution having a pH of about 5 to 6 and under salt concentration of about 0.25 to 0.35 M which favors selective binding of 2S canola protein to a cation-exchange medium to form a canola protein solution,
    separating the canola protein solution from residual canola oil seed meal,
    contacting the canola protein solution with the cation-exchange medium under conditions wherein the 2S canola protein is bound to the cation-exchange medium in preference to other canola proteins,
    separating the bound 2S canola protein from unbound canola proteins and impurities, and
    separating the bound 2S canola protein from the cation-exchange medium.

2. The method of claim 1, wherein the cation-exchange medium is in the form of resin beads or a membrane adsorber.

3. The method of claim 1 wherein said bound 2S protein is separated from the cation-exchange medium by contact of the cation-exchange medium with a saline solution of a concentration sufficient to break the bonds between the 2S protein and the ion-exchange medium.

4. The method of claim 3 wherein said saline solution used to separate the bound 2S protein from the cation-exchange medium has a salt concentration of about 0.55 to about 0.70 M.

5. A method of producing substantially pure 2S canola protein, which comprises:
    contacting canola oil seed meal with an aqueous salt solution having a sodium chloride concentration of about 0.25 to about 0.35 M to form an aqueous canola protein solution with a pH of about 5 to about 6,
    contacting said aqueous canola protein solution with a cation-exchange medium to bind 2S canola protein contained in said aqueous canola protein solution to said cation-exchange medium in preference to other canola proteins contained in said aqueous canola protein solution, including 7S and 12S canola proteins, and in preference to non-protein species contained in said aqueous canola protein solution, washing the cation-exchange medium to remove unbound canola proteins and impurities from the cation-exchange medium, contacting the washed cation-exchange medium with an aqueous salt solution having a sodium chloride concentration of about 0.55 to about 0.70 M to separate the bound 2S canola protein from the cation-exchange medium, collecting the separated 2S canola protein as an aqueous salt solution thereof, desalting the aqueous salt solution of the 2S protein, and drying the 2S protein.

6. The method of claim 5 wherein said cation-exchange medium is a membrane adsorber in which cation-exchange groups are bound to microporous membranes.

* * * * *